United States Patent [19]

Ryan et al.

[11] Patent Number: 4,695,582

[45] Date of Patent: *Sep. 22, 1987

[54] INHIBITORS OF ANGIOTENSIN CONVERTING ENZYME

[75] Inventors: James W. Ryan; Alfred Chung, both of Miami, Fla.

[73] Assignee: University of Miami, Coral Gables, Fla.

[*] Notice: The portion of the term of this patent subsequent to Sep. 1, 2004 has been disclaimed.

[21] Appl. No.: 116,950

[22] Filed: Jan. 30, 1980

Related U.S. Application Data

[63] Continuation of Ser. No. 941,289, Sep. 11, 1978.

[51] Int. Cl.$^4$ ............... A61K 31/40; A61K 31/41; C07D 207/00
[52] U.S. Cl. ................... 514/423; 548/531; 548/535
[58] Field of Search ............... 424/301; 514/255, 308, 514/423, 362, 363; 548/531, 535

[56] References Cited

U.S. PATENT DOCUMENTS

| | | | |
|---|---|---|---|
| 3,832,337 | 8/1974 | Ondetti et al. | 260/112.5 R |
| 3,865,934 | 2/1975 | Plotnikoff | 424/177 |
| 3,891,696 | 6/1975 | Bodor et al. | 260/112.5 R |
| 3,947,575 | 3/1976 | Ondetti | 424/177 |
| 3,973,006 | 8/1976 | Ondetti | 424/177 |
| 3,975,365 | 8/1976 | Mazur | 424/177 |
| 3,976,770 | 8/1976 | Bunspus et al. | 424/177 |
| 4,046,889 | 9/1977 | Ondetti et al. | 260/239 AR |
| 4,052,511 | 10/1977 | Cushman et al. | 424/244 X |
| 4,053,651 | 10/1977 | Ondetti et al. | 424/319 |

FOREIGN PATENT DOCUMENTS

2457463 6/1976 Fed. Rep. of Germany ...... 424/177

*Primary Examiner*—Delbert R. Phillips

[57] ABSTRACT

The compounds, N-[3-(benzoylphenylalanylthio)-2-D-methylpropanoyl]-L-proline (I), N-(2-benzoylphenylalanylthiopropanoyl)-L-proline (II) and N-(3-benzoylphenylalanylthiopropanoyl)-L-proline (III) are disclosed. These compounds are potent inhibitors of serum angiotensin converting enzyme.

15 Claims, No Drawings

INHIBITORS OF ANGIOTENSIN CONVERTING ENZYME

This is a continuation of application Ser. No. 941,289, filed Sept. 11, 1978.

BACKGROUND OF THE INVENTION

Angiotensin converting enzyme (peptidyldipeptide hydrolase, hereinafter referred to as ACE) occupies a central role in the physiology of hypertension. The enzyme is capable of converting the decapeptide angiotensin I, having the sequence AspArgValTyrIleHisProPheHisLeu to an octapeptide, angiotensin II by removal of the carboxyterminal HisLeu. The symbols for various chemical entities are explained in the following table:

Ala = L-alanine
Arg = L-arginine
Asp = L-aspartic acid
<Glu = pyro-L-glutamic acid
Gly = glycine
Hip = Hippuric acid (Benzoyl glycine)
His = L-histidine
Ile = L-isoleucine
Leu = L-leucine
Phe = L-phenylalanine
Pro = L-proline
Ser = L-serine
Trp = L-tryptophan
Tyr = L-tyrosine
Val = L-valine
γ-Glu = L-glutamic acid residue in peptide linkage at the γ-carboxyl group
ACE = Angiotensin converting enzyme
Hepes = N-2-hydroxyethylpiperazine-N'-2-ethanesulfonic acid Angiotensin I is formed by the action of the enzyme renin, an endopeptidase found in kidney, other tissues and plasma, acting on a serum α-2 globulin.

Blood pressure is affected by certain peptides found in the blood. One of these, angiotensin II, is a powerful pressor (blood pressure elevating) agent. Another, bradykinin, a nonapeptide with the sequence ArgProProGlyPheSerProPheArg is a powerful depressor (blood pressure lowering) agent. In addition to a direct presson effect, angiotensin II stimulates release of aldosterone which tends to elevate blood pressure by causing retention of extracellular salt and fluids. Angiotensin II is found in measurable amount in the blood of normal humans. However, it is found at elevated concentrations in the blood of patients with renal hypertension.

The level of ACE activity is ordinarily in excess, in both normal and hypertensive humans, of the amount needed to maintain observed levels of angiotensin II. However, it has been found that significant blood pressure lowering is achieved in hypertensive patients by treatment with ACE inhibitors. [Gavras, I., and Vukovich, R. A., *New Engl. J. Med.* 291, 817 (1974)].

ACE is a peptidyldipeptide hydrolase. It catalyzes the hydrolysis of the penultimate peptide bond at the C-terminal end of a variety of acylated tripeptides and larger polypeptides having an unblocked α-carboxy group. The peptide hydrolysis is represented diagramatically as: $R-A_2-A_1 + H_2O \rightarrow R-OH + H-A_2-A_1$, wherein $A_1$ is an amino acid at the carboxyl terminus of the peptide, $A_2$ is an amino acid linked to $A_1$ by a peptide bond, R is an N-substituted amino acid linked to $A_2$ by a peptide bond. The action of ACE results in hydrolytic cleavage of the penultimate peptide bond from the carboxyl-terminal end yielding as reaction products a dipeptide, $HA_2A_1$, and a remnant, $R-OH$.

The reactivity of the enzyme varies markedly depending on the substrate. At least one type of peptide bond, having the nitrogen supplied by proline, is not hydrolyzed at all. The apparent Michaelis constant (Km) varies from substrate to substrate over several orders of magnitude. For general discussion of the kinetic parameters of enzyme catalyzed reactions, see Lehninger, A., *Biochemistry*, Worth Publishers, Inc., New York, 1970, pp. 153–157. Many peptides which are called inhibitors of the enzymatic conversion of angiotensin I to angiotensin II are in fact substrates having a lower Km than angiotensin I. Such peptides are more properly termed competitive substrates. Examples of competitive substrates include bradykinin, and the peptide $BPP_{5\alpha}$ (also called SQ20475) from snake venom, whose sequence is <GluLysTrpAlaPro.

Numerous synthetic peptide derivatives have been shown to be ACE inhibitors by Ondetti, et al. in U.S. Pat. No. 3,832,337 issued Aug. 27, 1974.

The role of ACE in the pathogenesis of hypertension has prompted a search for inhibitors of the enzyme that could act as antihypertensive drugs. See for example U.S. Pat. Nos. 3,891,616, 3,947,575, 4,052,511 and 4,053,651. A highly effective inhibitor, with high biological activity when orally administered, is D-3-mercapto-2-methylpropanoyl-L-proline, designated SQ14225, disclosed in U.S. Pat. No. 4,046,889 to Ondetti et al., issued Sept. 6, 1977, and in scientific articles by Cushman, D. W. et al., *Biochemistry* 16 5484 (1977), and by Ondetti, M. et al., *Science*, 196 441 (1977). The inhibitor SQ14225 reportedly has an $I_{50}$ value of $2.3 \times 10^{-8}$M. The $I_{50}$ value is defined as a concentration of inhibitor required to produce 50% inhibition of the enzyme under a standard assay system containing an approximately $K_m$ level of substrate.

The mode of action of SQ14225 has been based upon a model of the active site of ACE developed by analogy with the berter known related enzyme, carboxypeptidase A. The active site was hypothesized to have a cationic site for binding the carboxyl end group of the substrate and a pocket or cleft capable of binding the side chain of the C-terminal amino acid and providing especially tight binding for the heterocyclic ring of a terminal proline residue. A similar pocket for the penultimate amino acid residue was postulated, and the published data suggested a rather stringent steric requirement, since the D-form of the inhibitor was substantially more potent than its stereoisomer or the 3-methyl and unsubstituted analogs. The sulfhydryl group on the inhibitor, postulated to be bound at the active site near the catalytic center, was believed to play a central role in inactivation of the enzyme by combining with the zinc moiety known to be essential for catalytic activity. Substituents on the sulfhydryl, such as a methyl group, and an S-acetyl derivative, substantially reduced potency of the inhibitor. See Cushman, D. W., et al., *Biochemistry*, supra.

In vitro study of the mechanism by which SQ14,225 and its analogs act to inhibit ACE has been somewhat hampered by the instability of these molecules under ambient conditions. For example, it has been observed that a fresh aqueous solution of concentration, e.g., 1 mg per ml of SQ14,225 at a pH of about 8 becomes substantially less active upon standing for as little as 30 minutes, and that activity continues to decrease as the solution stands for longer periods. It is believed that this loss in activity is mainly the result of dimerization of SQ14,225 occurring at the sulfhydryl end groups, whereby a disulfide is formed which is largely inactive as an inhibitor. Since the free sulfhydryl group is highly reactive and may be readily oxidized to polar acidic moieties such as sulfone and sulfoxide groups, it may also be that the observed in vitro loss of activity of aqueous solutions of SQ14,225 on standing is in some part a consequence of one or more such oxidation reactions, with formation of a sulfone or sulfoxide which does not function effectively as an inhibitor for ACE.

Such reports of SQ14,225 clinical testing as are currently available, some of which refer to the compound under the name "Captopril", suggest that the product is sufficiently stable in the normal gastric and intestinal environments of most patients to be an effective inhibitor for ACE when administered orally. It is not yet clear, however, whether there may be a group of patients for which SQ14,225 is substantially ineffective. Because of the high reactivity of the free sulfhydryl group, SQ14,225 could readily form mixed disulfides with serum, cellular proteins, peptides or other free sulfhydryl group-containing substances in the gastric or intestinal environments, in addition to the possibility for dimer formation or oxidative degradation reactions. A mixed disulfide with protein may be antigenic and, indeed, occasional allergic reactions have been clinically observed. See Gavras, et al., *New England J. Med.* 298, 991 (1978). Disulfides and oxidative degradation products of SQ14,225, if formed, may at best be expected to be largely ineffective as inhibitors. It may be hypothesized accordingly that dose response to SQ14,225 may vary with conditions of administration and among individual patients. Moreover, in at least some patients, unwanted side effects may occur or maintenance of an effective concentration of the inhibitor in the body may be difficult to control.

Thiolester compounds generally are thought to be highly reactive in that the thiolester linkage is readily hydrolyzable to a sulfhydryl moiety and a carboxylic moiety. Thiolesters are accordingly often used as active ester intermediates for acylation under mild conditions. Such groups as, e.g., acetylthio have been used as blocking groups in the above cited Ondetti, et al. patents. Thiolester intermediates are also postulated to occur in the biosynthesis of cyclic peptides such as tyrocidin or gramicidin S. See Lipmann, F. in *Accounts Chem. Res.* 6, 361 (1973).

It is accordingly of particular significance that the inhibitors of this invention, albeit thiolesters, appear to be exceptionally stable in vitro and relatively inert to oxidation. For example, it has been observed that solutions at approximately 1 mg per ml concentration, of an inhibitor of this invention, at pH levels of from about 7 to about 9.5 at room temperature in the presence of sodium bicarbonate give no color response to a selective staining agent for free sulfhydryl groups even after standing for two hours, thereby indicating stability to hydrolysis of the thiolester linkage.

Because of this observed in vitro stability, it is ized that the inhibitors of this invention may be effective in environments where SQ14,225 is largely ineffective or may be capable of administration under less rigorously controlled conditions.

SUMMARY OF THE INVENTION

The present invention provides three highly effective inhibitors of ACE withthe potential for being orally effective antihypertensive drugs. These compounds are N-[3-(benzoylphenylalanylthio)-2-D-methyl-propanoyl]-L-proline, hereinafter (I), N-(2-benzoylphenylalanylthiopropanoyl)-L-proline, hereinafter (II), and N-(3-benzoylphenylalanylthiopropanoyl)-L-proline, hereinafter (III). Unless noted otherwise, the proline moieties are in their L-forms.

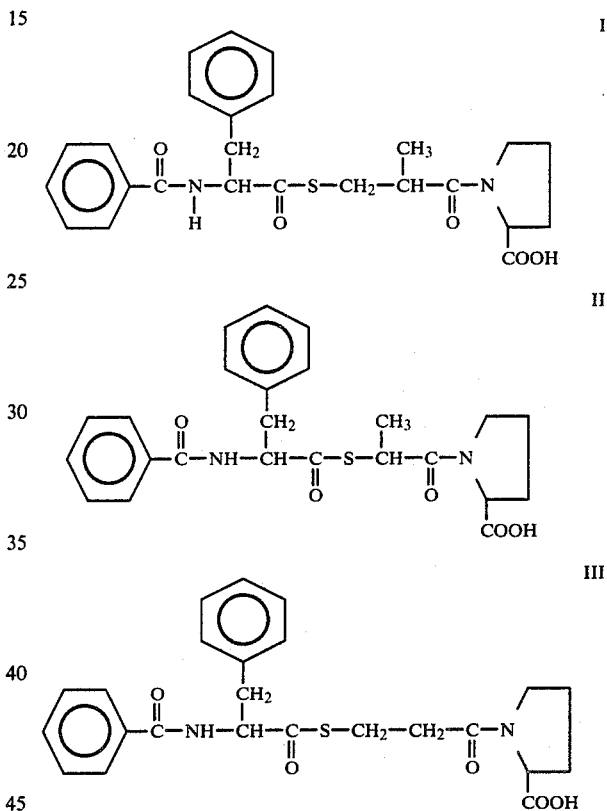

The unexpected uneffectiveness of the foregoing compounds provides insight into new and hitherto unrecognized properties of the binding and catalytic sites of ACE and of the nature of thiol ester compounds. The data presented herein supports a view that the enzyme possesse substrate recognition sites for groups on both sides of the bond to be hydrolyzed, including groups lying on that side of the susceptible bond distal from the free carboxyl group. Further, it appears that when such groups are incorporated into the inhibitor molecule, optimum binding is not as critically dependent upon the number and arrangement of carbon atoms in the penultimate amino acid or analog thereof, as was previously thought. Third, the presence of sulfur in thiol ester linkage is not deleterious to inhibitory potency, and the thiol ester compounds of the type disclosed are sufficiently stable to serve as orally effective antihypertensive agents.

The disclosed compounds appear to be orally effective inhibitors of serum ACE in those mammals having angiotensin-mediated blood pressure regulation, as shown by experiments in rabbits and rats. The in vivo effectiveness of ACE inhibition is considered predictive of effectiveness as oral depressor (anti-hypertensive) agents as demonstrated herein. Details of human therapeutic effectiveness will be unavailable until clinical testing is performed.

DETAILED DESCRIPTION OF THE INVENTION

Details of the synthesis and operational effectiveness of the foregoing compounds are described by the following examples.

EXAMPLE 1

A. ACE activity assay. For most experiments described herein, the enzyme was assayed in 0.05M Hepes buffer, pH 8.0 containing 0.1M NaCl and 0.75M $Na_2SO_4$. The substrate employed was Benzoyl-GlyHisLeu at a final concentration of $1 \times 10^{-4}$M, together with about 130,000 cpm of [$^3$H]-Benzoyl GlyHisLeu (25 Ci/mmole). Enzyme was diluted in the above buffer such that 40 µl buffered enzyme was capable of hydrolyzing 13% of substrate in a 15-minute incubation at 37° C. To initiate the assay, 40 µl of enzyme and 10 µl of water or inhibitor dissolved in water were preincubated for five minutes at 37° C. Substrate, 50 µl, was then added to initiate reaction and the solution was incubated for 15 minutes at 37° C. To terminate the reaction, 1 ml of 0.1M HCl was added, following which 1 ml of ethyl acetate was added. The mixture was agitated on a rotary mixer and centrifuged briefly to separate the phases.

An aliquot, 500 µl, of the ethyl acetate layer was transferred to a liquid scintillation vial containing 10 ml of Riafluor, trademark New England Nuclear Corporation, Boston, Mass. For determination of $I_{50}$ values, enzyme activity in the presence of inhibitor at a series of different concentrations was compared to activity in the absence of inhibitor A plot of inhibitor concentration versus percent inhibition yielded the $I_{50}$ value.

B. In certain experiments, as identified, an alternative assay system was employed using [$^3$H]-HipGlyGly as substrate as described by Ryan, J. W., et al., *Biochem J.* 167 501 (1977).

EXAMPLE 2

Using the assay system of Example 1A, a series of peptide substrates or substrate analogs was tested for inhibitor potency. Results are given in Table I.

TABLE I

| Compound | $I_{50}$* |
| --- | --- |
| L-proline | $1 \times 10^{-3}$ M |
| Ala—Pro | $1 \times 10^{-5}$ M |
| benzoyl-Phe | $4 \times 10^{-4}$ M |
| Phe—Ala—Pro | $2 \times 10^{-7}$ M |
| benzoyl-Phe—Ala—Pro | $1 \times 10^{-7}$ M |

The results illustrate the importance of providing recognition groups on both sides of the bond to be hydrolyzed by ACE.

A series of peptides and analogs in which L-cysteine was incorporated as the penultimate amino acid was tested for inhibitory effectiveness. Results are shown in Table II.

TABLE II

| Compound | $I_{50}$* |
| --- | --- |
| L-cysteine | $2 \times 10^{-4}$ M |
| Cys—Pro | $1.1 \times 10^{-5}$ M |
| γGlu—Cys—Pro | $1.1 \times 10^{-5}$ M |
| γGlu—Cys—Gly (glutathione) | $4 \times 10^{-5}$ M |
| acetyl-Cys—Pro | $5 \times 10^{-6}$ M |
| <Glu—Cys—Pro | $4 \times 10^{-6}$ M |
| benzoyl-Phe—Cys—Pro | $6 \times 10^{-7}$ M |
| benzoyl-Gly—Cys—Pro | $5 \times 10^{-7}$ M |

These data provide support for the conclusion that a free sulfhydryl group is not essential for inhibitory potency when the inhibitor, or competitive substrate, is tightly bound to the active site of the enzyme.

EXAMPLE 3

Preparation of ACE from guinea pig or human urine

Fresh urine was ultrafiltered using a membrane (PTGC 142 05, Millipore Corp., Bedford, MA, U.S.A.) with a 10,000MW retention limit. Typically, 500 ml of urine was ultrafiltered to approx. 15 ml and then the concentrated proteins were washed with water and then applied to a column (2.5×110 cm) of Sephacryl S-200, Trademark, Pharmacia Chemical Co.. Uppsala, Sweden, previously equilibrated with 0.05 M TrisHCl buffer, pH 8.0, with 0.5M NaCl. Under these conditions, ACE was eluted in two peaks; one, the major peak, was eluted just after the void volume ($V_e/V_o=1.21$) and the second (up to 20% of the total activity) at $V_e/V_o 1.41$. Enzyme activity was measured using [$^3$H]-HipGlyGly as described in Example 1B. Activities of both peaks were inhibited 30 completely by SQ 14,225 at 0.1 µM. The activities were inhibited to a maximum of 84% by antibody to guinea pig lung angiotensin converting enzyme. The enzyme used herein was that of the first peak to emerge from the Sephacryl column. The enzyme preparation was concentrated about 10-fold by ultrafiltration. In one such experiment, the concentrated urinary protein solution obtained by ultrafiltration contained 2,400 munits of enzyme at 8.0 munits/mg of protein, and peak 1 from the Sephacryl column contained 1,100 munits at 814 munits/mg of protein. Disc gel electrophoresis, at pH 9.0, of 28 µg of the final preparation showed four bands after staining with Coomassie blue. One band (Rf=0.21 in respect to bromophenol blue) corresponded to ACE.

EXAMPLE 4

Preparation of N-Benzoyl-D,L-Phenylalanine

A mixture containing 8.21 g of L-Phenylalanine, 5.565 g of $Na_2CO_3$ in 40 ml of water and 20 ml of tetrahydrofuran (THF) was stirred at room temperature. Benzoyl chloride, 7.73 g, dissolved in 20 ml of anhydrous THF, was added gradually over a period of 45 minutes with continued stirring at room temperature. Stirring was allowed to continue for an additional hour, at which time the reaction mixture was transferred to a rotary evaporator at 30° C. to remove the THF. An excess of water was then added and the reaction mixture extracted four times with ethyl acetate. The aqueous phase was then titrated to pH 2 with 3N HCl. A white crystalline precipitate formed which was recovered by filtration, washed three times with cold dilute HCl and three times with cold water, and dried in a vacuum oven over $P_2O_5$ at about 50° C. The product was recrystallized from aqueous 30 ethanol, yielding 8.37 g, m.p. 183° C.-184° C., which migrated as a single compound on thin layer chromatography in five separate solvent systems.

EXAMPLE 5

Preparation of N-Benzoyl-Phenylalanine-N-hydroxy-Succinimide ester 1.347 g. of Benzoyl-Phenylalanine and 0.576 g of N-hydroxy succinimide were mixed in a 1:1 (by volume) mixture of THF and dimethylformamide (DMF). The mixture was incubated at 4° C. overnight in the presence of 1.133 g of dicyclohexylcarbodiimide.

The reaction mixture was filtered and the solvent was removed under reduced pressure at 30° C. A white residue remained which was recrystallized from THF-isopropyl alcohol to yield 1.194 g (65.2%) of a white solid, m.p. 156° C.-157° C. The infrared absorption spectrum in chloroform showed bands at 3440 $cm^{-1}$ indicating an NH group, at 1818 $cm^{-1}$, 1790 $cm^1$, and 1744 $cm^{-1}$, characteristic of the N-carboxy succinimide group and at 1669 $cm^{-1}$, characteristic of the N-Benzoyl moiety.

EXAMPLE 6

Identification of thiol ester compounds

In the following examples, reaction products were frequently separated by thin layer chromatography. The thiol ester compounds were identified using chlorine/o-tolidine reagent which gives a cream colored spot. Compounds containing free sulfhydryl groups react with phenazine methosulfate to yield a reddish-orange color at room temperature. See *Anal. Biochem.* 79, 610 (1977). The thiol ester compounds require heating at 80° C. for 5-10 minutes to yield an orange color. Some solvent systems, for example, benzene/acetic acid/$H_2O$, 9:9:1, reduce color development of the thiol ester compounds.

EXAMPLE 7

Preparation of 2-Acetylthiopropanoic acid (Acetylthiolactic acid)

Commercial thiolactic acid was vacuum distilled under 1 mm Hg pressure. The fraction boiling between 94° C.-95° C. was collected. The reaction mixture was prepared by adding 105 g of $KHCO_3$ and 50 ml of water together with 100 ml of ether, cooling the mixture in an ice bath to 0° C.-5° C. with vigorous stirring. Approximately 50 mmoles thiolactic acid was added. Acetic anhydride, 47 ml (0.5 moles) was added dropwise over a period of one-half hour following which the reaction mixture was maintained at 0° C.-5° C. for another one-half hour. The reaction mixture was then slowly warmed to room temperature with stirring for one hour and cooled in an ice bath, after which 95 ml of concentrated HCl was added slowly. The mixture was extracted four times with 50 ml portions of ethyl ether. The collected ether phase was washed twice with a small amount of water and twice with saturated NaCl, then dried over anhydrous $MgSO_4$. Solvent was then removed with a rotary evaporator under high vacuum at 35° C. White crystals resulted which were purified by recrystallization from ethanol and n-hexane. The purified white crystalline material had a melting point of 50° C.-51.5° C. Infrared analysis in chloroform revealed an absorption band at 1135 $cm^{-1}$, indicative of the thiolester group, and carbonyl bands at 1690 and 1715 $cm^{-1}$. The product migrated as a single substance in thin layer chromatography in three solvent systems.

EXAMPLE 8

Preparation of 3-acetylthiopropanoic acid

The procedure described in Example 7 was followed except that the starting material was 3-mercaptopropanoic acid.

EXAMPLE 9

Preparation of 3-Acetylthio-2-methyl propanoic acid

The named compound was prepared by reacting 50 g of thioacetic acid with 40.7 g of methacrylic acid, heated on a steam bath for 1¼ hr. and allowed to stand at room temperature for 21 hours. The product was vacuum distilled under 1 mm Hg and the fraction boiling at 121° C.-122° C. was collected. The foregoing procedure yielded 57.2 g of light yellow oil. The infrared spectrum in chloroform was similar to that of 2-acetyl thiopropanoic acid.

EXAMPLE 10

Preparation of 3-acetylthiopropanoyl-L-proline-t-butyl ester

The product of Example 8, 3-acetylthiopropanoic acid, 0.865 g, was dissolved in 2 ml redistilled THF and cooled to 0° C. A cooled solution of dicyclohexylcarbodiimide, 1.2031 g in 2 ml of THF was added, following which a cooled solution of L-proline-t-butyl ester, 1 g, was added. The reaction mixture was stored at 0° C. for one hour, then at 4° C. overnight. The reaction mixture was then filtered and the precipitate was washed with ethyl acetate. Solvents of the filtrates were removed under reduced pressure in a rotary evaporator. The residue was dissolved in ethyl acetate which was then washed three times with cold 1N citric acid, twice with saturated NaCl, twice with cold 1N $NaHCO_3$ and three times with saturated NaCl. The solution was dried over anhydrous $MgSO_4$ and filtered. The solvent was removed under reduced pressure in a rotary evaporator at 30° C. yielding a white clear oily product in approximately 87% yield. The product migrated as a single spot in thin layer chromatography in five solvent systems.

EXAMPLE 11

Synthesis of 3-mercaptopropanoyl-L-proline-t-butyl ester

The product from Example 10, 3-acetylthiopropanoyl-L-proline-t-butyl ester, 0.5 g, was mixed with 4.5 ml of 5.5N methanolic ammonia at room temperature under nitrogen for one hour. The solvent was then removed at 25° C. with a rotary evaporator. After the product was taken up in methanol and reevaporated twice more in the rotary evaporator, the clear oily residue was dissolved in ethyl ether, washed twice with 5% potassium bisulphate and once with saturated NaCl, dried over $MgSO_4$ and filtered. Residual solvent was removed in vacuo to yield a clear oily product, migrating as a single spot on thin layer chromatography in three separate solvent systems.

EXAMPLE 12

Preparation of N-(3-benzoylphenylalanylthiopropanoyl)-L-proline-t-butyl ester

The oily product from Example 11, 3-mercaptopropanoyl-L-proline-t-butyl ester was mixed with 245 mg of 1-Hydroxybenzotriazole (HOBt) and 1 ml of redistilled DMF in an ice bath at 0° C. A solution of 608 mg of N-Benzoyl-Phenylalanyl-N-hydroxy-succinimide ester in 2 ml redistilled DMF was added and the mixture was stirred under nitrogen for one hour, then allowed to stand at room temperature for 40 hours. The reaction was terminated with the addition of 25 μl of N,N-dimethyl-1,3-propanediamine. Solvent was removed under high vacuum at 35° C. Ethyl acetate, 50 ml, was added, and the solution was washed twice with saturated NaCl, three times with 1N sodium bicarbonate and three times with saturated NaCl. The solution was then dried over anhydrous magnesium sulphate and filtered. The solvent was removed yielding 0.725 g of a clear gum-like product. The product appeared to be about 90% pure as judged by thin layer chromatography in four solvent systems.

EXAMPLE 13

Preparation of (III), N-(3-benzoylphenylalanylthiopropanoyl)-L-proline

The product of Example 12 was deprotected by reaction with trifluoroacetic acid in anisole. The reaction mixture was incubated at room temperature for one hour, following which trifluoroacetic acid and anisole were removed in vacuo at 32° C. The reaction mixture was then partitioned between saturated NaHCO$_3$ and ethyl acetate in the cold. The bicarbonate phase was washed twice with ethyl acetate and once with ether. Then, in the presence of ethyl acetate, the bicarbonate phase was acidified with HCl, and, after extraction, the ethyl acetate phase was collected and washed with saturated NaCl, dried over anhydrous MgSO$_4$ and filtered. The solvent was removed under reduced pressure. The product was further purified by chromatography on Sephadex G-25, trademark Pharmacia Company, Uppsala, Sweden, using a 1.2 cm×96 cm column eluted with butanol:acetic acid:water, 4:1:5 (volume ratio). 2.20 me fractions were collected. Most of the product was found in fractions 21 through 23 as determined by positive reaction with o-tolidine/chlorine reagent and with phenazine methosulfate at pH 5.

EXAMPLE 14

Synthesis of compound (II), N-(2-benzoylphenylalanylthiopropanoyl)-L-proline

Synthesis of compound (II) was accomplished by essentially the same process as described in Examples 10–13, using 2-acetyl-thiopropanoic acid described in Example 7, as starting material.

EXAMPLE 15

Synthesis of compound (I), N-[3-(benzoylphenylalanylthio)-2-D-methyl-propanoyl]-L-proline A reaction mixture containing 93.3 mg of 2-D-methyl-3-mercaptopropanoyl-L-proline, 62 mg of HOBt, 165 mg of N-benzoylphenylalanyl-N-hydroxy-succinimide ester, prepared as described in Example 5, was cooled in an ice bath at approximately 0° C., after which 0.0544 ml of N-ethyl morpholine was added. The reaction mixture was stirred in an ice bath for three hours, incubated at 4° C. overnight, then at room temperature for twenty hours. The reaction was terminated by the addition of 25 μl of N,N-dimethyl-1,3-propanediamine, and stirred for an additional two hours. Ethyl acetate was added to the reaction mixture which was then washed by extraction with cold 0.1N HCl, followed by two washes with water and three washes with saturated NaCl. The mixture was then dried over anhydrous MgSO$_4$ and filtered. The solvent was removed under reduced pressure in a rotary evaporator, yielding a clear, oily product.

The product was purified by chromatography on a column of Sephadex LH20, 1.2 cm×96 cm. The column was eluted with THF, and 2.5 ml fractions were collected. Fractions 30 and 31 were pooled and yielded, after solvent removal under high vacuum, 110 mg of product. Anhydrous ether was added and a white gum-like material was obtained. The ether was decanted and the white gum-like material was dissolved in THF and transferred to a vial, dried in a stream of nitrogen, then further dried over P$_2$O$_5$ overnight. A foam-like product, 82 mg, was obtained.

Fractions 29, 32 and 33 were rechromatographed under identical conditions. Fractions 33 through 36 of the second chromatography were pooled, worked up as described and yielded an additional 51 mg of product. Total yield was 71%.

EXAMPLE 16

Synthesis of 2-benzoylphenylalanylthiopropanoic acid

A solution of 2.6935 g of Benzoyl-Phenylalanine in 30 ml of redistilled DMF was cooled to −20° C. A solution of 1,1'-carbonyldiimidazole in 10 ml redistilled DMF was added dropwise with vigorous stirring. Temperature was not allowed to exceed −14° C. Following the addition, the solution was stirred at −10° C. for two hours. D,L-Thiolactic acid, 1.12 g in 5 ml of redistilled DMF previously neutralized with 1.43 ml of redistilled N-ethylmorpholine was then added with continued stirring at −10° C. for one hour. The solution was then slowly warmed to room temperature. About 50 ml ethyl acetate was added. The mixture was then cooled and neutralized with 1 ml of concentrated HCl in approximately 10 ml saturated NaCl. The organic phase was then washed three times with subsaturated NaCl, i.e., 5 ml saturated NaCl diluted with 1 ml water. Occasionally, a three layer system was observed. In such cases, the middle layer was saved and combined with the lower aqueous phase. The organic phase was dried over anhydrous MgSO$_4$, filtered and placed in the rotary evaporator to remove solvent. A small amount of yellowish oil that was not the desired product was recovered. The combined aqueous phase and middle phase were acidified at 0° C. with concentrated HCl to pH 2, and extracted three times with ethyl acetate and the organic phase was washed with saturated NaCl and dried over anhydrous MgSO$_4$, filtered and rotary evaporated. 3.33 g of clear oil was recovered. The material thus recovered was identified by its behavior on thin layer chromatography.

The resulting product, 2-benzoylphenylalanylthiopropanoic acid is a useful intermediate in the synthesis of (II). The D- and L- isomers may be resolved and then coupled to L-proline by conventional techniques. The other inhibitors described herein, compounds (I) and (III), may also be synthesized by the same strategy: formation of the benzoylphenylalanylthiopropanoyl derivative followed by resolution of stereoisomers where appropriate, followed by coupling to L-proline.

EXAMPLE 17

Synthesis of N-(2-benzoylphenylalanylthiopropanyl)-L-proline-t-butyl ester

The product of Example 16, 933 mg 2-benzoyl-phenylalanylthiopropanoic acid, was dissolved in 3 ml DMF and cooled to 0° C. in an ice-acetone bath. Dicyclohexylcarbodiimide, 536 mg in 1.5 ml DMF, was added and the mixture was stirred 5 minutes at 0° C. 462 mg of L-proline-t-butyl ester in 1.5 ml DMF was added. The reaction mixture was stirred at 4° C. overnight. The reaction mixture was worked up by addition of 10 ml ethyl acetate, filtration and addition of 20 ml ethyl acetate to the filtrate. The combined ethyl acetate fractions were chilled in a freezer, extracted three times with saturated NaCl, once with ice-cold 0.1N HCl, again three times with saturated NaCl, then three times with ice-cold cold 1N NaHCO$_3$, and three times with saturated NaCl. The organic phase was dried with anhydrous MgSO$_4$ and again filtered. Solvent was removed with a rotary evaporator under high vacuum, yielding 1 16 g of white residue. The product was substantially pure as judged by thin layer chromatography.

EXAMPLE 18

Synthesis of compound (II), N-(2-benzoylphenylalanylthiopropanoyl)-L-proline

The product of Example 17, N-(2-benzoyl-phenylalanylthiopropanoy L-proline-t-butyl ester, 1.25 g, was suspended in 4 ml anisole and with 8 ml trifluoroacetic acid for 1 hour at room temperature with stirring. In view of the fact that some starting material was later recovered, the reaction time should be increased. Trifluoroacetic acid was removed with a rotary evaporator under high vacuum. The residue was dissolved in 1 ml THF and chromatographed on a 2.2 cm×99 cm column of Sephadex LH-20 eluted with THF. Fractions of about 5.3 ml were collected. The product was eluted in fractions 41–43. The combined fractions 41–43 were evaporated to dryness, dissolved in a small amount of isopropanol and rechromatographed on a 1.2 cm×95 cm LH-20 column, eluted with isopropanol. Fractions of about 2.05 ml were collected. Fractions 48–50 contained 78 mg of the desired compound as an oil. Side fractions 46–47 and 51–53 were saved for rechromatography. The oil was dissolved in a small volume of THF in a vial, then the THF was evaporated under a stream of N$_2$. The vial was then placed in a round bottom flask connected to a rotary evaporator. After 3 hr under high vacuum, a stable, dry foam was obtained.

EXAMPLE 19

The inhibitory potency of compounds (I), (II) and (III) in vitro was measured in the assay system described in Example 1A. Results are shown in Table III.

TABLE III

| Compound | I$_{50}$ |
|---|---|
| SQ 14,225 | 3 × 10$^{-8}$ M |
| (I) | 4 × 10$^{-8}$ M |
| (I) | 1 × 10$^{-8}$ M |
| racemic (II) | 7 × 10$^{-8}$ M |
| racemic (II) | 4 × 10$^{-8}$ M |
| (III) | 7 × 10$^{-7}$ M |

The compound designated racemic (11) is N-[2(D,L)-benzoylphenylalanylthiopropanoyl]-L-proline. In view of the high degree of stereospecificity exhibited by the enzyme's interaction with SQ14225, it seems likely that only one of the stereoisomers of compound (II) is active. If so, the I$_{50}$ value for the active isomer will be half that of the racemic mixture. In view of the high degree of inhibitory potency exhibited by compound (II), it would appear that stereospecificity in the region of the thiopropanoyl analog is less critical than previously thought.

Thioester compounds (I), (II) and (III) have been found to be surprisingly resistant to alkaline hydrolysis. Compound (I) is not hydrolyzed at pH 9.5 in 1 M NaHCO$_3$. Therefore the observed inhibitory effects cannot be accounted for by postulating spontaneous hydrolysis of the thioester bond to regenerate the free sulfhydryl group. That such hydrolysis does not occur to an appreciable extent under assay conditions is further demonstrated by the extremely low inhibitory potency of acetyl SQ14225, previously published.

EXAMPLE 20

Oral effectiveness.

Female Sprague-Dawley rats, approximately 250 g weight, were fasted overnight and then administered either 0.5 ml of saline, via stomach tube, or 0.5 ml saline containing compound (I) at a dose of 1 mg per kg of body weight. At timed intervals the rats were beheaded using a guillotine and 3 ml-5 ml blood was collected. The sera were assayed for intrinsic ACE activity, using the assay of Example 1B. The results of duplicate runs are shown in Table IV.

TABLE IV

| Time (minutes after drug administration) | ACE activity (Percent of Control) Serum | |
|---|---|---|
| 5 | 100 | 100 |
| 10 | 65 | 52 |
| 30 | 50 | 45 |
| 60 | 50 | 42 |
| 90 | 20 | 20 |

The results indicate a substantial and consistent degree of oral effectiveness for compound (I).

EXAMPLE 21

Oral effectiveness of (I)

Young, unanesthetized rabbits, fasted overnight, weighing about 1 kg, were given compound (I). The compound was dissolved in water at alakline pH, 1 mg of (I) in 3 ml water containing 50 μl 1 N NaHCO$_3$. Blood samples, 0.5 ml, were collected at timed intervals from a marginal ear vein. Sera obtained after clot formation and centrifugation were assayed for intrinsic ACE activity, using 1 μl in the assay of Example 1A. Results are shown in Table V.

TABLE V

| Time after administration (hours) | Serum ACE activity Percent of Control | |
|---|---|---|
| | Rabbit 1 | Rabbit 2 |
| −0.1 (control) | 100 | 100 |
| 0.167 | 7 | 11 |
| 0.33 | 8 | 9 |
| 0.5 | 7 | 8 |
| 1.0 | 20 | 44 |
| 1.5 | 14 | 55 |
| 2.0 | 11 | 44 |
| 2.5 | 12 | 40 |
| 3.0 | 30 | — |
| 4.0 | 23 | — |
| 5.0 | 19 | — |
| 20.0 | 70 | — |

The compound was therefore highly effective in duplicate trials In addition, the long-term effectiveness suggests that compound (I) is relatively stable in vivo, a desirable property for an anti-hypertensive therapeutic agent.

EXAMPLE 22

Oral effectiveness of (I)

Rats (210–290 g body weight) were fasted overnight and then anesthetized with intraperitoneal pentobarbital, 50–60 lrg/kg. Tracheostomy was performed and the animals were ventilated mechanically. A cannula was inserted into a femoral vein for injection of angiotensin I or II, and a second cannula was inserted into a common carotid artery for direct measurement of arterial blood pressure. Heparin, 1,000 units, was injected via the femoral vein to prevent coagulation. Blood pressure was measured with a pressure transducer connected to a polygraph. The rats were injected with 80 ng of angiotensin I or Angiotensin II in 20 μl of 0.9 g % NaCl; an amount of angiotensin I or II sufficient to raise mean arterial blood pressure by 27–40 mm Hg. After the responsiveness of a given rat to angiotensins I and II was established, compound(I), at 2 or 5 mg/kg (drug dissolved in 0.5 ml of H2O plus 10 μl of 1N NaHCO3), was given via a stomach tube. At timed intervals, the effects of 80 ng of angiotensin I or angiotensin II on means arterial blood pressure were tested. Results are shown in Table VI.

TABLE VI

| Time After Oral Administration of (I) (minutes) | Blood Pressure Response to 80 ng of Angiotensin I | | |
|---|---|---|---|
| | Drug at 5 mg/kg | | Drug at 2 mg/k |
| | Rat 1 | Rat 2 | Rat 3 |
| | (values in % of control) | | |
| −6 | 100% | 100% | 100% |
| +6 | — | 67 | 111 |
| 12 | 41 | 57 | 93 |
| 18 | 36 | — | 81 |
| 24 | — | 43 | 85 |
| 35 | 23 | 37 | 56 |
| 48 | 18 | 17 | — |
| 58 | 23 | 17 | 56 |
| 68 | — | 20 | 52 |
| 78 | — | 17 | — |
| 88 | — | 13 | 30 |
| 118 | 23% | — | 37 |
| 138 | — | — | 60 |
| 148 | — | — | — |
| 169 | — | — | 37 |
| 185 | — | 27 | 37 |
| 205 | — | 33 | 44% |
| 213 | — | 33 | |

TABLE VI-continued

| Time After Oral Administration of (I) (minutes) | Blood Pressure Response to 80 ng of Angiotensin I | | |
|---|---|---|---|
| | Drug at 5 mg/kg | | Drug at 2 mg/k |
| | Rat 1 | Rat 2 | Rat 3 |
| 226 | 43% | | |

Compound (I) was highly effective inhibiting the pressor effects of angiotensin I even in rats anesthetized with pentobarbital, a substance which decreases gatrointestinal motility and which may interfere with gastrointestinal absorption. For a discussion of the pharmacological effects of barbiturates, see Goodman, L. S. and Gilman, A., *The Pharmacological Basis of Therapeutics*, The Macmillan Co., New York, 1965, pp. 105–128. In addition, a graded dose-response is evident: Compound (I) at 5 mg/kg is clearly more effective than compound (I) at 2 mg/kg. At either dosage, the duration of drug action was long (>226 minutes), a desirable property for a compound to be used to confer therapeutic benefit in hypertensive cardiovacular disease.

The effects of compound (I) were specific. The pressor effects of angiotensin I were inhibited by compound (I) but the effects of angiotensin II were not inhibited. As is well-known, angiotensin I does not raise arterial blood pressure without first being converted to angiotensin II (as through the action of angiotensin converting enzyme).

EXAMPLE 23

Oral effectiveness of (II)

Rate were prepared as described in Example 22. Compound (II) N-(2-benzoyl-D,L-phenylalanylthiopropanoyl)-L-proline was given orally, via a stomach tube, at a dose of 12 mg/kg or 20 mg/kg. Compound (II) was dissolved in 0.5 ml of H2O plus 10μl of 1N NaHCO3. In all other respects, the experimental preparations were exactly as described in Example 22. Results are shown in Table VII.

TABLE VII

| Time After Oral Administration of (II) (minutes) | Blood Pressure Response (% of Control) to 80 ng of Angiotensin I | |
|---|---|---|
| | Drug at 12 mg/kg Rat 1 | Drug at 20 mg/kg Rat 2 |
| −8 | 100% | 100% |
| +6 | 109 | 91 |
| 12 | 80 | 70 |
| 23 | — | 76 |
| 30 | 51 | 76 |
| 38 | — | — |
| 47 | 71 | — |
| 56 | 69 | 55 |
| 76 | 63 | 40 |
| 95 | — | 40 |
| 101 | — | — |
| 142 | — | 76 |
| 150 | 49 | — |
| 158 | 57% | 76 |
| 166 | | 76 |
| 176 | | 76% |
| 184 | | |

Thus, in addition to compound (I), compound (II) is also effective when given orally in sufficient dosage. Compound (II) is also specific: It inhibited the pressor effects of angiotensin I but did not inhibit the pressor effects of angiotensin II.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What we claim is:

1. New compounds selected from the group: N-[3-(benzoylphenylalanylthio)-2-D-methylpropanoyl]-L-proline, N-(2-benzoylphenylalanylthiopropanoyl)-L-proline and N-(3-benzoylphenylalanylthiopropanoyl)-L-proline.

2. The compond N-3-(benzoylphenylalanylthio)-2-D-methylpropnaoyl) L-proline.

3. The compound N-(2-benzoylphenylalanylthiopropanoyl)-L-proline.

4. The compound N-(3-benzoylphenylalanylthiopropanoyl)-L-proline.

5. A method for reducing serum angiotensin converting enzyme in a mammal comprising administering orally to a mammal in need of such treatment an effective dose of an angiotensin converting enzyme inhibitor selected from the group consisting of N-[3-(benzoylphenylalanylthio)-2-D-methyl-propanoyl]-L-proline, N-(2-benzoylphenylalanylthiopropanoyl)-L-proline and N-(3-benzoylphneylalanylthiopropanoyl)-L-proline.

6. The method of claim 5 wherein the inhibitor is N-[3-(benzoylphenylalanylthio)-2-D-methylpropanoyl]-L-proline.

7. The method of claim 5 wherein the inhibitor is N-(2-benzoylphenylalanylthiopropanoyl)-L-proline.

8. The method of claim 5 wherein the inhibotor is N-(3-benzoylphenylalanylthiopropanoul)-L-proline.

9. A method for lowering mammalian blood pressure comprising administering orally to a mammal having elevated blood pressure an effective dose of a compound selected from the group consisting of N-[3-(benzoylphenylalanylthio)-2-D-methylprpanoyl-L-proline, N-(2-benzoylphenylalanylthiopropanoyl)-L-proline and N-(3-benzoylphenylalanylthiopropanoyl)-L-proline.

10. The method of claim 9 wherein the compound is N-[3-(benzoylphenylalanylthio)-2-D-methylpropanoyl]-L-proline.

11. The method of claim 9 wherein the compound is N-(2-benzoylphenylalanylthiopropanoyl)-L-proline.

12. The method of claim 9 where the compound is N-(3-benzoylphenylalanylthiopropanoyl)-L-proline.

13. A compound having the structure

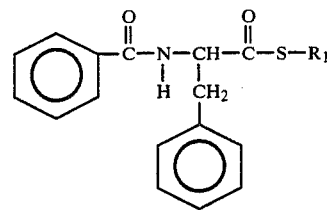

wherein $R_1$ is selected from the group consisting of

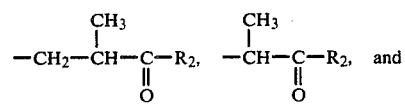

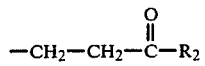

and $R_2$ is a proline moiety.

14. An orally effective composition for inhibting serum angiotensin converting enzyme comprising an inhibitor according to claim 1 togetherf with a pharmaceutically acceptable carrier.

15. An orally effective depressor composition comprising an inhibitor of angiotensin converting enzyme according to claim 1 together with a pharmaceutically acceptable carrier.

* * * * *

UNITED STATES PATENT AND TRADEMARK OFFICE
CERTIFICATE OF CORRECTION

PATENT NO. : 4,695,582

DATED : September 22, 1987

INVENTOR(S) : James W. Ryan and Alfred Chung

It is certified that error appears in the above-identified patent and that said Letters Patent is hereby corrected as shown below:

Cover page, Col 2 - Insert the following omitted U.S. Patent Documents:

| | | |
|---|---|---|
| 4154840 | 3/1978 | Ondetti |
| 4070361 | 4/1977 | Petrillo |
| 4091024 | 12/1976 | Ondetti |
| 4108886 | 3/1977 | Ondetti |
| 4116692 | 12/1976 | Ondetti |

UNITED STATES PATENT AND TRADEMARK OFFICE
CERTIFICATE OF CORRECTION

PATENT NO. : 4,695,582

DATED : September 22, 1987

INVENTOR(S) : James W. Ryan and Alfred Chung

It is certified that error appears in the above-identified patent and that said Letters Patent is hereby corrected as shown below:

| | | |
|---|---|---|
| 4129566 | 12/1978 | Ondetti |
| 4146611 | 12/1977 | Ondetti |
| 4179568 | 7/1978  | Cohen et al. |
| 4154934 | 8/1978  | Bernstein |
| 4154935 | 9/1978  | Ondetti |
| 4165776 | 12/1976 | Ondetti |
| 4105789 | 5/1976  | Ondetti |
| 4151172 | 7/1978  | Ondetti |
| 4154937 | 6/1978  | Cushman |
| 4129571 | 10/1977 | Ondetti |
| 4206122 | 4/1978  | Natarajan |
| 4192878 | 5/1978  | Ondetti |
| 4179434 | 6/1978  | Ondetti et al. |
| 4173704 | 5/1978  | Ondetti et al. |
| 4112119 | 3/1977  | Ondetti et al. |

UNITED STATES PATENT AND TRADEMARK OFFICE
CERTIFICATE OF CORRECTION

| | |
|---|---|
| PATENT NO. : | 4,695,582 |
| DATED : | September 22, 1987 |
| INVENTOR(S) : | James W. Ryan and Alfred Chung |

It is certified that error appears in the above-identified patent and that said Letters Patent is hereby corrected as shown below:

| | | |
|---|---|---|
| 4127729 | 2/1978 | Ondetti |
| 4128721 | 3/1978 | Ondetti |
| 4140786 | 3/1978 | Ondetti et al. |
| 4140797 | 3/1978 | Ondetti et al. |
| 4140864 | 3/1978 | Ondetti et al. |
| 4154736 | 2/1978 | Ondetti et al. |
| 4154936 | 3/1978 | Ondetti et al. |
| 4154942 | 8/1978 | Ondetti et al. |
| 4154960 | 6/1978 | Ondetti et al. |
| 4156084 | 8/1978 | Ondetti et al. |
| 4156786 | 6/1978 | Ondetti et al. |
| 4284780 | 5/1978 | Ondetti et al. |
| 4339600 | 2/1978 | Ondetti et al. |
| 4154946 | 6/1978 | Ondetti et al. |
| 4165320 | 6/1978 | Ondetti et al. |

UNITED STATES PATENT AND TRADEMARK OFFICE
CERTIFICATE OF CORRECTION

PATENT NO. : 4,695,582
DATED : September 22, 1987
INVENTOR(S) : James W. Ryan and Alfred Chung It is certified that error appears in the above-identified patent and that said Letters Patent is hereby corrected as shown below:

Cover page, Col 2 - Insert the following:

OTHER PUBLICATIONS

Cronyn et al., J. Am. Chem. Soc., 74:4726 (1952).
Fischer et al., Ber 33: 2383 (1900).
Fisher et al., FEBS Letters, 107:273 (1979).
Lehninger A., Biochemistry, pp. 189-194 (1975).
Ryan, J. W. et al, Biochem. J., 167:501 (1977).
Methoden der Organischem Chem (Houben-Weyl), vol. XV,
   Pt. 1, p. 376 et seq.
   Pt. II, p. 1 et seq., (1974).
Carter et al., J. Biol. Chem 138:627, (1941).
Engel et al., Proc. Soc. Exp. Biol. Med 143:483, 1973).
Jager et al., Chem. Ber. 103, 1727, (1970).
Klosterman et al., Biochem 6, 170, (1967).
Lijinski et al., Tetrahedron 26, 5137, (1970).
Nagasawa et al., J. Med. Chem. 16,583 (1973).
Mita et al., Chem. Pharm. Bull. 26, (4), 1333-1335,
   (1978).
Kripalani et al., Clin. Pharmacol. Ther. 27(5), 636-641,
   (1980).

UNITED STATES PATENT AND TRADEMARK OFFICE
CERTIFICATE OF CORRECTION

PATENT NO. : 4,695,582
DATED : September 22, 1987
INVENTOR(S) : James W. Ryan and Alfred Chung It is certified that error appears in the above-identified patent and that said Letters Patent is hereby corrected as shown below:

Pfister et al., J. Am. Chem. Soc. 71,1096, (1949).

Merrified, Adv Enzymol 32,221, (1969).

Ricci et al., Anal Biochem. 79,610 (1977).

Cushman, D. W. et al., Progr. Cardiovacs. Dis. 21, 176, (1978).

Oparil et al., Circ. Res. 32,415, (1973).

Oparil et al., Circ. Res. 29,682, (1971).

Dorer et al., Biochem. J. 141,915 (1974).

Sharpless, S.K., "Hypnotics and Sedatives", The Pharmacological Basis of Therapeutics, The Macillan Co., (1965), pp. 105-128.

Kripalani, K. J. et al., Abstracts, Joint Meeting of ASPET/SOT, Aug. 13-17, 1978.

Singhvi, S. M. et al., Abstracts, Joint Meeting of ASPET/SOT, Aug. 13-17, 1978.

Wong, K. K. and Dreyfuss, J., Abstracts, Joint Meeting of ASPET/SOT, Aug. 13-17, 1978.

Buxton et al., J. Chem. Soc., p. 366, (1954).

Col 1, line 29 - delete "L-phenylalamine" and insert -- phenylalanine --

UNITED STATES PATENT AND TRADEMARK OFFICE
CERTIFICATE OF CORRECTION

PATENT NO. : 4,695,582
DATED : September 22, 1987
INVENTOR(S) : James W. Ryan and Alfred Chung It is certified that error appears in the above-identified patent and that said Letters Patent is hereby corrected as shown below:

Col 3, line 66 - delete "ized" and insert in its place -- hypothesized --

Col 6, line 33 - delete "30"

Col 11, line 27-28 - delete "yielding 1 16g" and insert -- yielding 1.16g --

Col 11, line 36 delete "and with 8ml" and insert -- and reacted with 8 ml --

Col 13 line 28 delete "1rg/kg" and insert in its place -- mg/kg --

Col 14, line 34 delete "Rate" and in its place insert -- Rats --

Signed and Sealed this

Sixteenth Day of May, 1989

Attest:

DONALD J. QUIGG

Attesting Officer

Commissioner of Patents and Trademarks